United States Patent [19]

Williams

[11] Patent Number: 4,769,854
[45] Date of Patent: Sep. 13, 1988

[54] KICKING SPAT

[76] Inventor: James L. Williams, R.R. 1, Box-356, Sand Springs, Okla. 74063

[21] Appl. No.: 60,343

[22] Filed: Jun. 10, 1987

[51] Int. Cl.$^4$ ............................................. A41D 13/00
[52] U.S. Cl. ...................................... 2/22; 128/80 H; 128/893
[58] Field of Search ................. 2/22, 239; 36/1.5, 2 R; 128/80 D, 80 H, 153

[56] References Cited

U.S. PATENT DOCUMENTS

| | | | |
|---|---|---|---|
| 3,515,136 | 6/1970 | Baker | 2/22 X |
| 3,721,237 | 3/1973 | Alessio | 128/153 X |
| 4,084,586 | 4/1978 | HeHick | 128/80 H X |
| 4,280,488 | 7/1981 | Polsky et al. | 128/80 H |
| 4,313,433 | 2/1982 | Cramer | 128/80 H |
| 4,495,942 | 1/1985 | Palumbo | 128/80 H |
| 4,527,556 | 7/1985 | Nelson | 128/80 H |
| 4,590,932 | 5/1986 | Wilkerson | 128/80 H X |

Primary Examiner—Louis K. Rimrodt
Assistant Examiner—J. Olds

[57] ABSTRACT

A single piece of medium thickness and quality leather trimmed into a shape which allows for a first portion to be wrapped tightly around the ankle covering the lower leg and for a second portion to be wrapped tightly around the foot covering the instep. The two wraps are held tight by joining separate sets of loop pile and cooperative hook fastener strips which are sewn to the leather. The ankle portion is dressed by placing the inside strip of the ankle fastener facing outward on the outside of the ankle and rotating the wrap around the backside, inside and front side of the ankle overlapping the beginning point where the outside strip of the fastener is joined to the inside strip. The foot portion is dressed by placing the inside strip of the foot fastener facing outward on the outside of the foot and rotating the wrap around the bottom side, inside and topside of the foot overlapping the beginning point where the outside strip of the fastener is joined to the inside strip. The ankle portion holds the foot portion in place. The foot portion provides a target on the instep to kick a ball.

3 Claims, 1 Drawing Sheet

U.S. Patent  Sep. 13, 1988  4,769,854
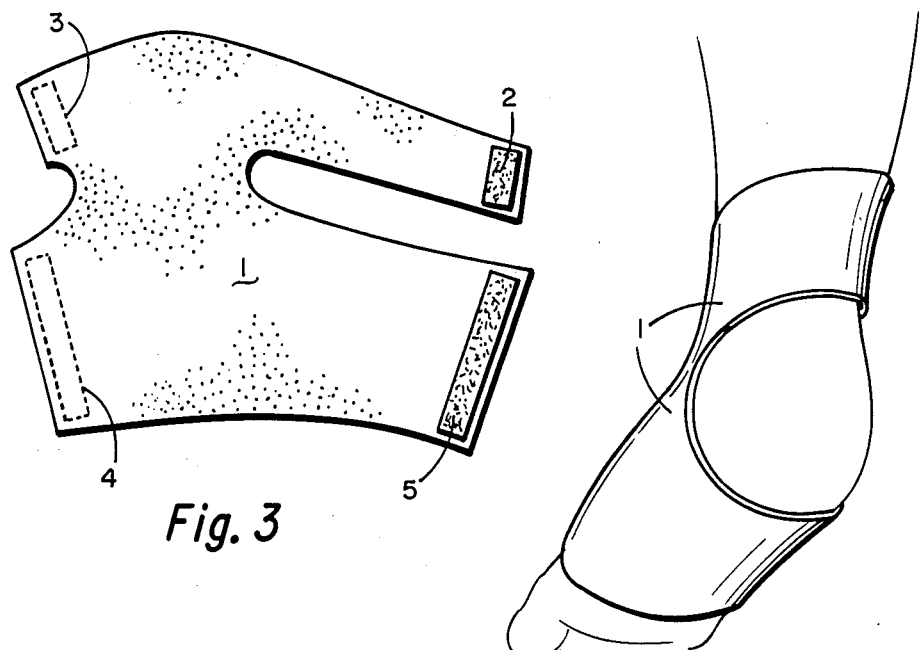
Fig. 3
Fig. 1
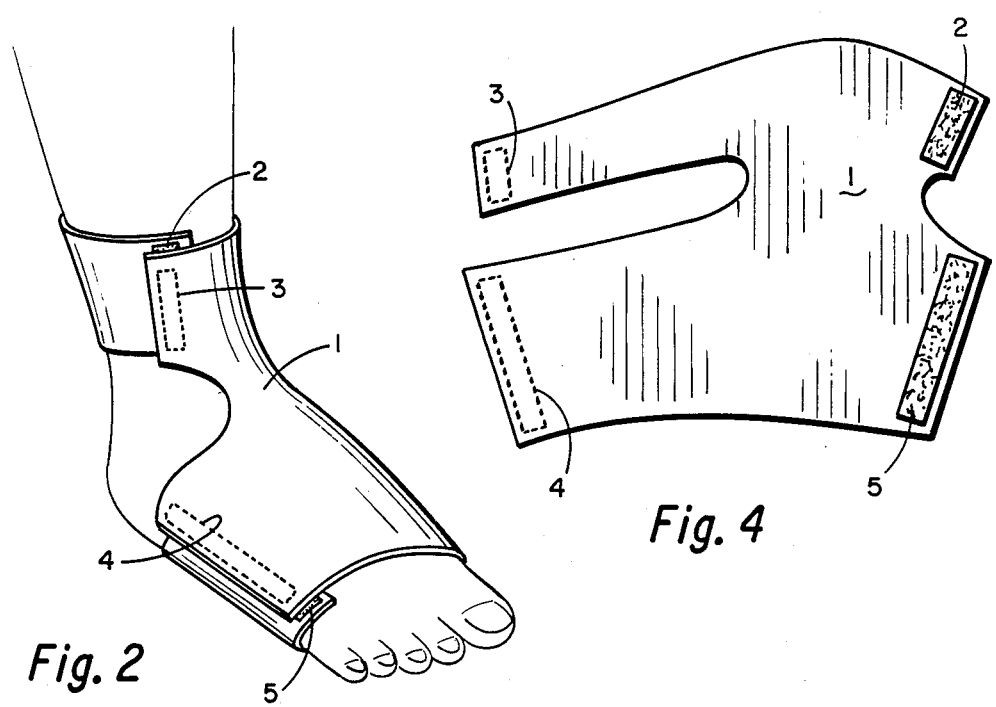
Fig. 2
Fig. 4

KICKING SPAT

BACKGROUND OF THE INVENTION

The rules in American style football provide for two distinct kinds of kicks. One is called a place kick and the other is called a punt. A place kick is, as the name implies, where the the ball is first placed and then kicked. Punts are kicks which are not placed. The types of place kicks are the kick off, the field goal and the conversion kick. Although punting has remained rather constant through the history of football, place kicking has seen several improvements. Early on, the drop kick method of scoring a field goal requiring the kicker to take the snap, drop the ball to the ground and time his foot to kick the ball just as the point of the ball touched the ground was abandoned in favor of a more carefully placed kick. This method included a traditional straight on and in line with the goal post approach to the ball. More recently, the traditional straight on approach to the ball was made obsolete by a side approach. The straight on approach produces a high trajectory path for the ball whereas the side approach produces a low trajectory path therefore resulting in a longer distance kick. By using the instep, the side approach eliminated the use of the toes to kick the ball and therefore made it possible to kick the ball with a bare foot. Almost every kick in football is made with such intense force that the bare toes will suffer severe injury if they come in contact with the ball or any other object during the kick. The three main advantages in using the barefoot method to kick a ball are (1) to be able to arch the foot in such a way as to stiffen the instep, (2) the improved speed at which the lightened foot can be directed and controlled, and (3) the smooth, unobstructed and accurate feeling produced by the bare foot making contact with the ball. The barefoot kick in football is performed with such risk that it requires some measure of dare. It is very similar to the martial art technique of breaking a board with a bare hand.

The use of the kicking spat improves the barefoot method to kick a ball by providing a more safe and accurate target to make contact with the ball without any loss of advantage, especially while learning this method.

BRIEF SUMMARY OF THE INVENTION

A piece of leather trimmed into a spat like shape and attached to the ankle area of the lower leg and covering the foot area over the instep and held tightly wrapped by loop pile and cooperative hook fastener strips sewn to the leather thus improving the safety and accuracy of a person using the barefoot method to kick a ball. The ankle portion is put on the lower kicking leg by placing the inside strip of the ankle fastener facing outward on the outside of the ankle and rotating the wrap around the backside, inside and front side of the ankle overlapping the beginning point where the outside strip of the fastener is joined to the inside strip. The foot portion is put on the kicking foot by placing the inside strip of the foot fastener facing outward on the outside of the foot and rotating the wrap around the bottom side, inside and topside of the foot overlapping the beginning point where the outside strip of the fastener is joined to the inside strip. The ankle portion provides a very slight brace to the lower leg and holds the foot portion in place. The foot portion provides a very slight brace to the instep and provides an improved target for the foot to make contact with a ball without eliminating any other aspect of a bare foot kick. The otherwise bare foot is allowed to arch, stiffen and move at the same speed and control as though it were still bare. The kicking spat provides an improvement for both a place kick and a punt.

BRIEF DESCRIPTION OF THE DRAWINGS

FIG. 1 is an inner, lower and rear view of a bare foot with the kicking spat fastened in place.

FIG. 2 is an outer, upper and front view of a bare foot with the kicking spat fastened in place.

FIG. 3 is a upright, unwrapped and flattened view of the ball contact side of the kicking spat displaying the pattern.

FIG. 4 is a upright, unwrapped and flattened view of the foot contact side of the kicking spat displaying the pattern.

DETAILED DESCRIPTION

In the drawings, the invention has been illustrated with a lower leg and foot on the right side of the body. It should be understood that the invention is applicable to the left side of the body in mirror image. Also, the invention has been illustrated with loop pile and cooperative hook fasteners. It should also be understood that the invention is applicable to other forms of fasteners including laces and buckled straps.

Referring to the drawings in detail wherein like numerals designate like parts:

FIG. 1 shows the kicking spat 1, at an angle from inside, underneath and the rear of the lower leg and foot. The kicking spat fits tightly up against the body parts.

FIG. 2 shows the kicking spat 1, at an angle from outside, above and the front of the lower leg and foot. The kicking spat fits tightly up against the body parts and is held tight by two sets of loop pile and cooperative hook fastener strips sewn to the leather. Both sets of strips are joined and fastened together in FIG. 2. One set of strips are for the ankle 2 and the other set of strips are for the foot 5. The outer ankle fastener strip is sewn to the spat with leather craft thread 3. The outer foot fastener strip is sewn to the spat with leather craft thread 4. The fasteners consist of two different kinds of strips, one being loop pile strip and the other being a cooperative hook strip. Either kind of strip may be sewn to either part of the spat as long as the strips cooperate with each other when fastened. The fasteners should overlap in a front over back and top over bottom fashion so as to be aerodynamic when the lower leg and foot are passing through the air on the final power kicking stroke.

FIG. 3 is an unfastened, unwrapped and flattened upright view of the kicking spat 1, displaying the pattern from the ball contact side, which is the finished side of the leather. The locations of the inner parts of the strip fasteners 2 and 5 are shown. The locations of the outer parts of the strip fastener threads 3 and 4 are shown.

FIG. 4 is an unfastened, unwrapped and flattened upright view of the kicking spat 1, displaying the pattern from the foot contact side, which is the unfinished side of the leather. The locations of the inner parts of the strip fastener threads 3 and 4 are shown. The locations of the outer parts of the strip fasteners 2 and 5 shown.

It should be understood that the apparatus, as drawn and described, may require alteration in form without departing from the spirit of the invention or the scope of the following claims:

I claim:

1. A kicking aid for attachment to a foot of a kicker to provide a defined preferable area of impact, comprising:
   a pliable spat member including:
   a pair of opposed upper flaps and a pair of opposed lower flaps defining opposed horizontal cut-out areas threbetween;
   the upper flaps adapted to be placed around the foot above an ankle portion of the foot;
   the lower flaps adapted to be placed around an instep portion of the foot to provide a defined preferable area of impacct, and with the ankle portion of the foot disposed within the cut-out areas; and
   means for removable connecting the upper flaps one to another and for removably connecting the lower flaps one to another;
   wherein the means for removably connecting the lower flaps is disposed away from an upper surface of the instep portion of the foot and toes on the foot extend outwardly from the kicking aid.

2. A kicking aid of claim 1 wherein a first of the upper flaps is longer than a second flap of the pair, and a first of the lower flaps is longer than a second flap of the pair.

3. A kicking aid of claim 1 wherein the means for removably connecting the flaps comprises strips of loop pile and cooperative hook fastener strips.

* * * * *